US00PP22168P3

(12) United States Plant Patent
Allen, III

(10) Patent No.: US PP22,168 P3
(45) Date of Patent: Sep. 27, 2011

(54) ***ZOYSIAGRASS* NAMED 'ALOYZIA'**

(50) Latin Name: *Zoysia japonica*
Varietal Denomination: Aloyzia

(76) Inventor: Charles H. Allen, III, Sarasota, FL (US)

( * ) Notice: Subject to any disclaimer, the term of this patent is extended or adjusted under 35 U.S.C. 154(b) by 0 days.

(21) Appl. No.: 12/655,027

(22) Filed: Dec. 22, 2009

(65) Prior Publication Data

US 2011/0154550 P1 Jun. 23, 2011

(51) Int. Cl.
*A01H 5/00* (2006.01)

(52) U.S. Cl. ..... Plt./390

(58) Field of Classification Search ..... Plt./390
See application file for complete search history.

(56) References Cited

U.S. PATENT DOCUMENTS

PP11,537 P 10/2000 Sweet

*Primary Examiner* — Susan McCormick Ewoldt
(74) *Attorney, Agent, or Firm* — Gifford, Krass, Sprinkle, Anderson & Citkowski, P.C.

(57) ABSTRACT

A new and distinct variety of *Zoysia* grass, substantially characterized by its distinctive dark green color, its tolerance to winter climate, and its spreading growth pattern.

3 Drawing Sheets

Latin name: *Zoysia japonica.*
Varietal denomination: 'Aloyzia'.

The parent of 'Aloyzia' *Zoysia* grass is Meyer *Zoysia* grass. 'Aloyzia' differs from its parent in that it is a deeper, greener color. It has a finer texture and is much more aggressive than Meyer *Zoysia* grass. It also grows more upright than its parent.

FIELD OF THE INVENTION

The invention is directed to a new variety of *Zoysia* grass and more particularly a grass that exhibits a deeper green color and better cold tolerance than *Zoysia* grass.

BACKGROUND OF THE INVENTION

The invention herein is a new and distinct variety of *Zoysia* grass. I discovered this plant in a lawn planted at my home in Exeter, R.I. in the mid to late nineteen forties to early fifties by my father, Charles H. Allen Jr. The original planting was Meyer *Zoysia*. Some of it survived until the 1960s In May 2006 I planted what was left in six flats and took them with me when I moved to Florida in November 2007.

This grass began to exhibit qualities distinctly different from other types of *Zoysia* and other warm weather grasses here in Florida. This grass has a medium texture, comparable to Kentucky Bluegrass varieties, but definitely finer texture than other *Zoysia* varieties such as Empire or Meyer. It also has exhibited deeper green color and better cold tolerance.

'Empire' '*Zoysia*' grass is the subject of U.S. Plant Pat. No. 11,466. "Meyer" *Zoysia* grass doesn't appear to have been patented. It was released by the U.S.D.A. in 1951.

I proceeded to send a sample to Dr. Rebecca Brown at the University of RI for a DNA test to verify whether or not it was a new variety. At the same time I expanded my new seedling by vegetative division using two to three node sections. I removed two inches of soil in front of my house, laid down weed fabric to prevent contamination from soil weeds, and replaced the soil with sand in which I planted the nodes. It took four months to become a solid strand of planting material. It was planted February 1st, was completely full by June 1st. The nodes were planted three-four inches apart in rows three to four inches apart. Growth characteristics exhibit greater rhizome activity and fill in empty spaces with more upright growth than typical *Zoysia* growth of stolons, which grow laterally. Consequently producing a tight upright growth with much better appearance. Dr. Rebecca Brown has confirmed the fact that I have a new variety of *Zoysia* that I have named Aloyzia.

Aloyzia has been maintained at 1½ inch height of cut, fertilized with a 4-1-2 ratio with interim applications of ½ lb N of Milorganite. It has received 1-1½ lb N per month during grow-in period.

As indicated above I performed asexual reproduction of my new Aloyzia by vegetative division in Sarasota Fla.

I have chosen "Aloyzia" as the varietal name for my new grass.

SUMMARY OF THE INVENTION

Aloyzia is a distinctive, new variety of *Zoysia* grass characterized by its upright growth habit, forming a medium textured, and tight, dark colored firm turf. These traits are maintained when propagated asexually.

DETAILED DESCRIPTION OF THE PREFERRED EMBODIMENTS

Figure 1:
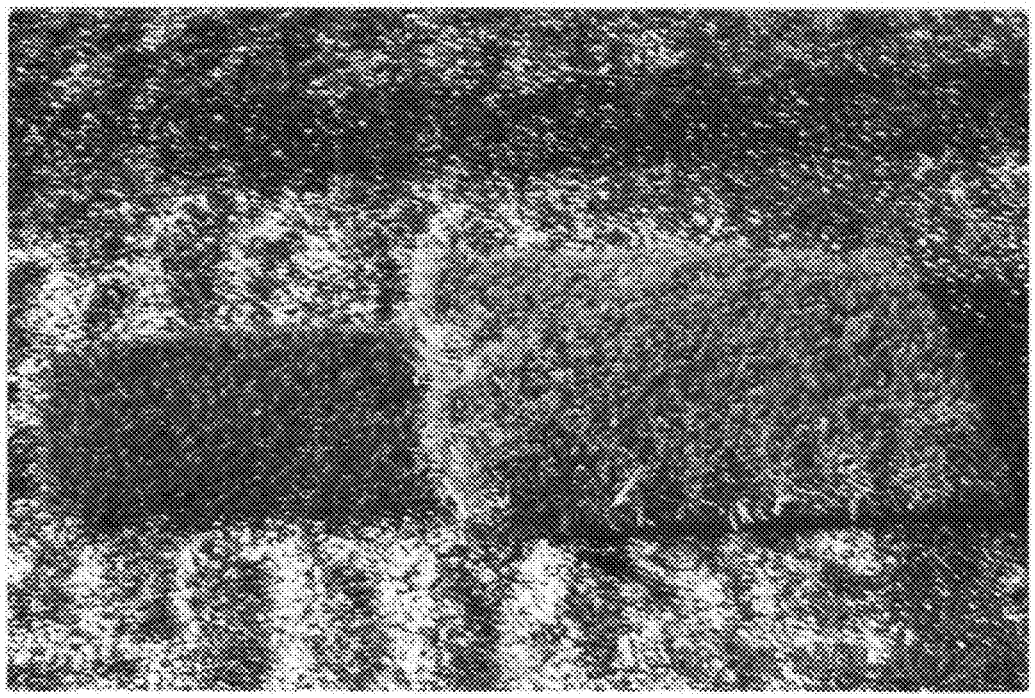
FIG. 1 shows the overall appearance of the grass of this invention. It includes a comparison with Empire *Zoysia* on the right to illustrate the more upright growth, darker color and overall tighter turf of Aloyzia shown on the left.
Figure 2:
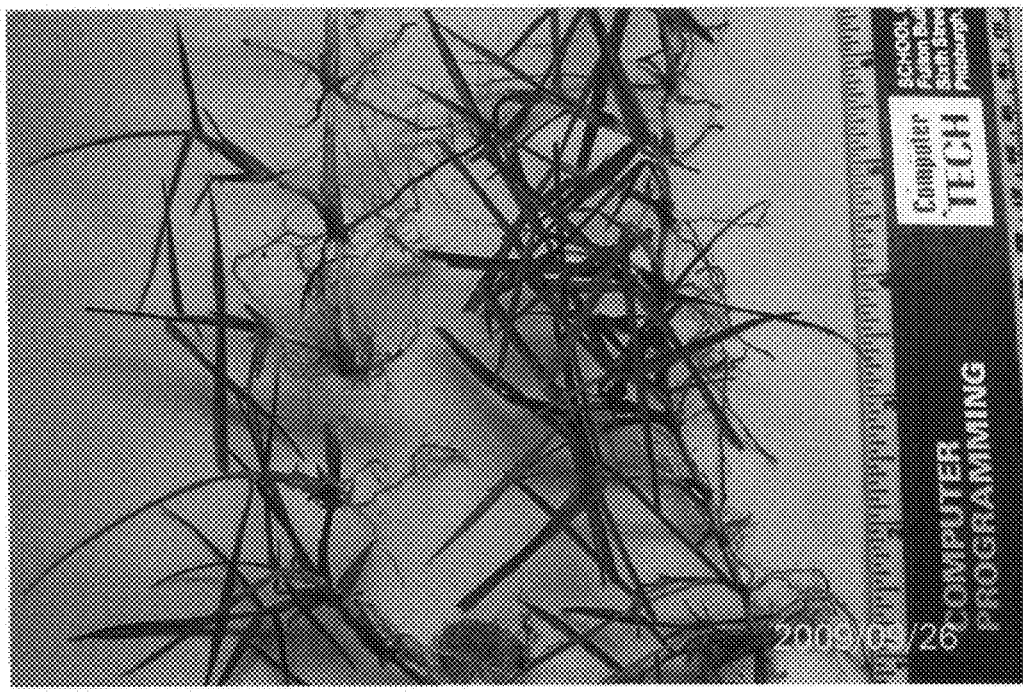
FIG. 2 shows a comparison of rhizomes/stolons of Empire *Zoysia* on the left with Aloyzia on the right. It illustrates the difference in diameter size, length of internodes and number of nodes per inch.
Figure 3:
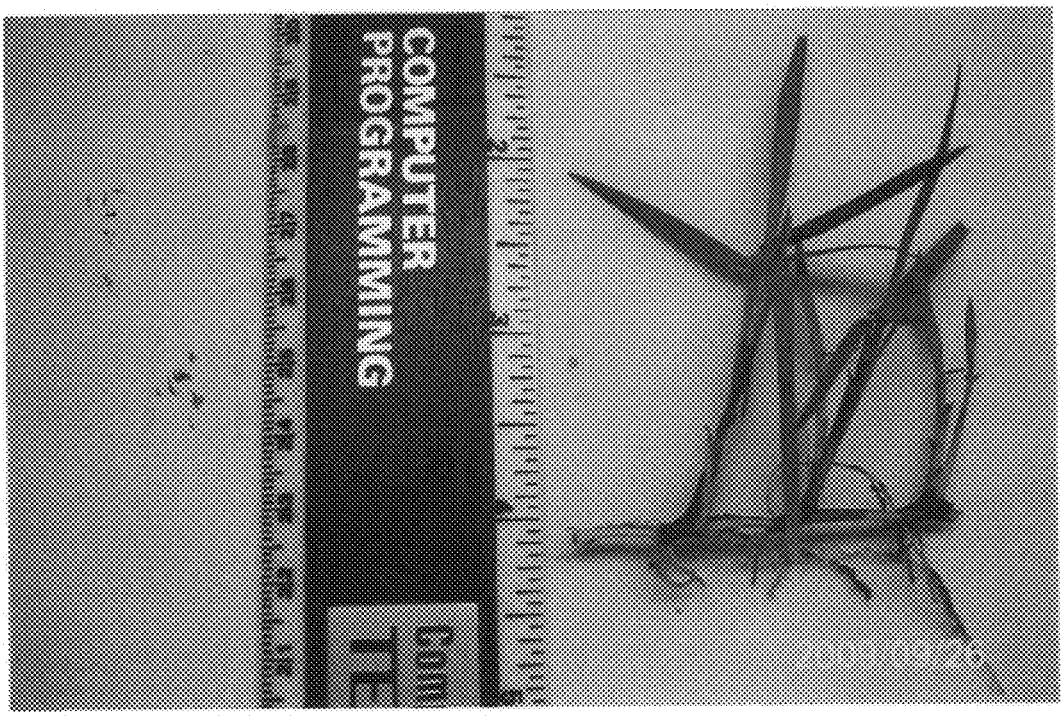
FIG. 3 illustrates the branching characteristics of the grass of this invention.
Figure 4:
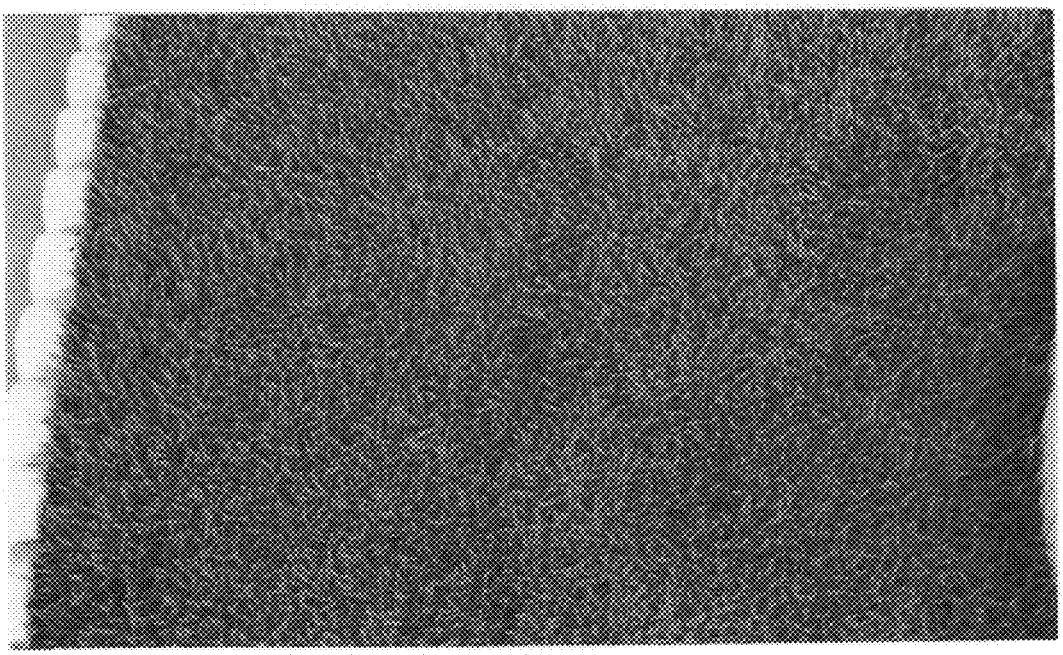
FIG. 4 shows a planting of Aloyzia grass illustrating the tightness of the turf.
Figure 5:
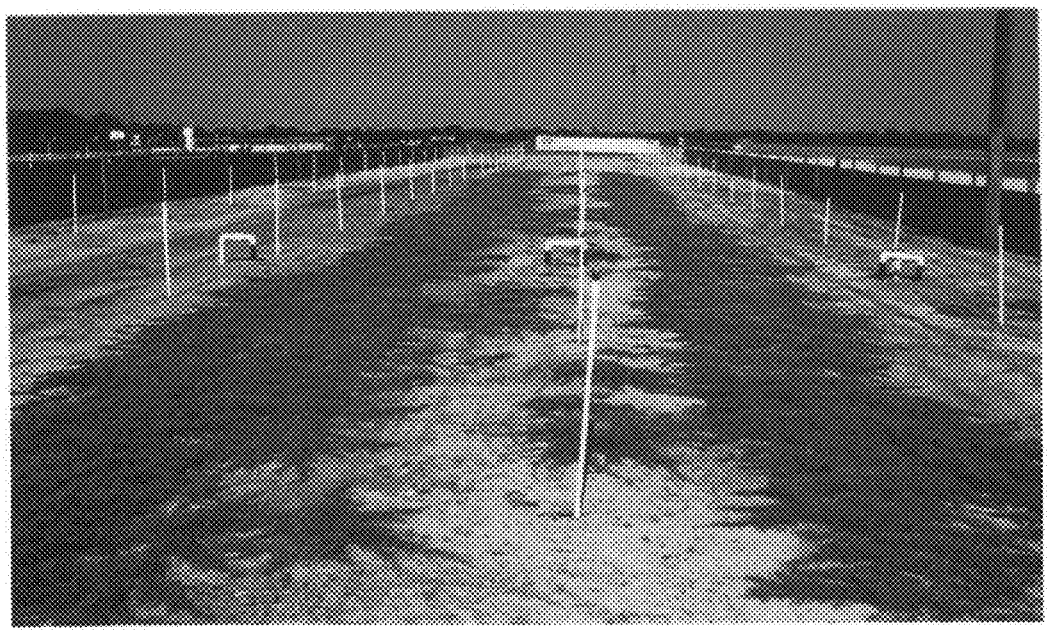
FIG. 5 illustrates the spreading characteristics of Aloyzia sprigged by a four-foot wide machine using 150 sq. ft. of nursery sod. Rows are approx 150 ft long w/approx 6 ft between rows. Total width nearly 20 ft wide. Also a good illustration of its color.

The following is a detailed description of the new grass variety, based upon my observations of the plant as grown in Sarasota, Fla.

"Aloyzia" is a perennial vegetatively propagated *Zoysia* grass. It grows by creeping or ascendant rhizomes/stolons which root at the nodes. Its color is a deeper green color than most other known varieties of *Zoysia.* I have asexually propagated the new grass in Sarasota Fla. by means of stolon/rhimzome cuttings containing one, two, three and more node sections. It has also been asexually propagated for evaluation in Arcadia, Fla., as well as other locations in Texas, Kentucky and Georgia. Planting stock has been grown, as shown in the illustrations, for use in studying performance and in comparison with other grasses to evaluate its viability for use in warm climate areas.

The growth habit of Aloyzia is fast growing and aggressive with many lateral shoots with increasing upright growth of leaf blades with increasing density producing a "firm" turf The internodes of Aloyzia will vary in length depending upon the height of cut. The nodes will range between ¼ in at a mowing height of 1½ in, and approx ½ inch apart for new-grown runners.

It should be apparent to one with ordinary skill in the art that I have described a new and distinct variety of *Zoysia* grass plant, Aloyzia, characterized by its green color, (#141 Strong Green—5.8g 4.4 8.7—#006B3C as defined by the ISCC-NBS centroid color chart). This new variety produces a faster establishment growth rate and a finer texture, and with an upright growth characteristic that produces less thatch/mat build-up. The florescence of the new variety of *Zoysia* grass plant is purplish in color. The stolons/rhizomes of the new variety of *Zoysia* grass plant are closer together producing more numerous plants than most other varieties of *Zoysia* that generally produce a much coarser texture. Aloyzia produces a medium textured turf very similar to the appearance of Kentucky Bluegrass with a darker green color than most *Zoysia* varieties.

SUMMARY

The grass of the present variety includes the following characteristics;

a. The upper surface of the leaf is an attractive dark green color, color number 141 Strong Green—5.8g 4.4 8.7—#006B3C, as defined by the ISCC-NBS centroid color chart of 2004. The lower surface of the leaf is also a deep green color defined by color number 142 Deep Green on the ISCC-NBS color chart of 2004. The margin is the color of the leaf.
b. The grass is low growing, erect in habit.
c. The grass grows by stolons and rhizomes, forming a dense, uniform surface, with an extensive root system. The stolons are #87 Light yellow—3.8y-7.1-6.5 #D79D41 as defined by ISCC-NBS centroid color chart. Nodes range between 1.25-1.5 mm apart.
d. Leaves rolled in the bud.
e. The leaf blade is flat and gradually tapering to an acute point.
f. The first mature leaf is approx 0.25 mm in width and 3.5-4 mm in length.
g. The leaf blade is glabrous.
h. The ligule is a very small ciliate fringe. Cilia are numerous with varied lengths that may range up to 0.25 mm in length.
i. Auricles are absent
j. The collar is continuous.
k. The sheath is glabrous, except for hairs at the top of the sheath at the ligule. The sheath is split with separate margins.
l. The entire plant is glabrous, except at the top of the sheath where there are cilia at the ligule.
m. The inflorescence consists of a single spike at the top of the main stem.
n. The spike contains stamen of a purplish color.

Having now described the new and distinct variety of *Zoysia* grass plant which I have discovered and asexually produced, I claim:

1. A new and distinct variety of *Zoysia* grass, substantially as herein illustrated and described, characterized by its distinctive combination of vegetative characteristics, its dark green color and its spreading growth pattern.

* * * * *